United States Patent [19]

Pelrine et al.

[11] Patent Number: 5,270,273

[45] Date of Patent: Dec. 14, 1993

[54] OLEFIN OLIGOMERIZATION CATALYST

[75] Inventors: Bruce P. Pelrine, Trenton; Kirk D. Schmitt, Pennington, both of N.J.; James C. Vartuli, West Chester, Pa.

[73] Assignee: Mobil Oil Corporation, Fairfax, Va.

[21] Appl. No.: 1,133

[22] Filed: Jan. 6, 1993

Related U.S. Application Data

[60] Continuation-in-part of Ser. No. 883,053, May 8, 1992, abandoned, which is a continuation of Ser. No. 802,105, Dec. 4, 1991, abandoned, which is a division of Ser. No. 693,254, Apr. 29, 1991, Pat. No. 5,105,051.

[51] Int. Cl.$^5$ ............................................. B01J 29/36
[52] U.S. Cl. ................................................... 502/60
[58] Field of Search .................. 502/60; 423/277, 718; 585/10

[56] References Cited

U.S. PATENT DOCUMENTS

| | | | |
|---|---|---|---|
| 4,743,437 | 5/1988 | Whittman | 502/60 |
| 4,827,064 | 5/1989 | Wu | 585/10 |
| 4,827,073 | 5/1989 | Bokers et al. | 376/439 |
| 5,012,020 | 4/1991 | Jackson et al. | 585/10 |
| 5,068,096 | 11/1991 | Valyocsik | 423/277 |
| 5,098,684 | 3/1992 | Kresge et al. | 423/277 |
| 5,102,643 | 4/1992 | Kresge et al. | 423/328 |
| 5,198,203 | 3/1993 | Kresge et al. | 423/718 |

Primary Examiner—Carl F. Dees
Attorney, Agent, or Firm—Alexander J. McKillop; Malcolm D. Keen

[57] ABSTRACT

A catalyst for oligomerizing alpha olefins to produce hydrocarbon oligomers useful as lubricants and lubricant additives comprises a supported reduced Group VIB metal, preferably chromium, in the form of its oxide. The support is a mesoporous, inorganic, crystalline solid of unique structure, of novel pore geometry. The preferred forms of these mesoporous materials are characterized by substantially uniform hexagonal honeycomb microstructure, with uniform pores having a cell diameter greater than 13 Å, preferably in the mesoporous range of about 20–100 Å. The use of the catalysts made with the mesoporous support materials enables products of greater viscosity to be made as compared to the products from catalysts using amorphous supports. The catalyst is usually used under oligomerization conditions at a temperature of about 90° to 250° C. to produce liquid hydrocarbon oligomers in the lubricant range which have a branch ratio of less than 0.19 and high values of viscosity index.

20 Claims, 2 Drawing Sheets

OLEFIN OLIGOMERIZATION CATALYST

CROSS-REFERENCE TO RELATED APPLICATIONS

This application is a continuation-in-part of Ser. No. 07/883,053, filed May 8, 1992 (now abandoned), which is a continuation of Ser. No. 802,105, filed Dec. 4, 1991 (now abandoned) which, in turn is a divisional of Ser. No. 07/693,254, filed April 29, 1991, now U.S. Pat. No. 5,105,051.

This support materials for the catalysts described in this application are described in related U.S. Pat. Nos. 5,102,643 and 5,098,684 and Application Ser. No. 07/734,825 now U.S. Pat. No. 5,198,203.

Field of the Invention

This invention relates to catalysts which are useful for producing olefin oligomers which are useful as lubricant basestocks and lubricant additives.

Background of the Invention

Efforts to improve upon the performance of natural mineral oil based lubricants by the synthesis of oligomeric hydrocarbon fluids have been the subject of important research and development in the petroleum industry for a large number of years and have led to the introduction of a number of superior polyalpha-olefin (PAO) synthetic lubricants produced by the oligomerization of alpha-olefins or 1-alkenes. In terms of lubricant property improvement, the thrust of the industrial research effort on synthetic lubricants has been toward fluids exhibiting useful viscosities over a wider range of temperature, i.e., improved viscosity index(VI), while also showing lubricity, thermal and oxidative stability and pour point equal to or better than mineral oil. These new synthetic lubricants exhibit lower friction characteristics and are therefore capable of increasing mechanical efficiency of various types of equipment including engines, transmissions, worm gears and traction drives, doing so over a wider range of operating conditions than mineral oil lubricants.

Notwithstanding their generally superior properties, PAO lubricants are often formulated with additives to enhance those properties for specific applications. Among the more commonly used additives are oxidation inhibitors, rust inhibitors, metal passivators, antiwear agents, extreme pressure additives, pour point depressants, detergent-dispersants, viscosity index (VI) improvers, foam inhibitors and the like. This aspect of lubricant technology is described in Kirk-Othmer "Encyclopedia of Chemical Technology", 3rd Edition, Vol. 14, pp. 477–526, to which reference is made for a description of the use of such additives.

Improvements in synthetic lubricant technology have resulted both from new additive developments intended to address deficiencies in the lubricant (oligomer) basestocks as well as from developments in new base fluid (oligomer). Recently, lubricant compositions (referred to in this specification as HVI-PAO) of remarkable high VI coupled with low pour point have been developed. These lubricant compositions are described in U.S. Pat. Nos. 4,827,064 and 4,827,073, to which reference is made for a detailed description of these lubricants, methods for their preparation and of their properties and uses. These HVI-PAO materials comprise polyalpha-olefin oligomers prepared by the use of a reduced metal oxide, preferably reduced chromium, oligomerization catalyst. The lubricant product is characterized by a branch ratio less than 0.19, indicating a high degree of linearity and pour point below $-15°$ C. In its as-synthesized form, the HVI-PAO oligomer has olefinic unsaturation associated with the last of the recurring monomer units in the structure and this can be removed by a simple hydrogenative treatment to produce a stabilized, fully saturated oligomer product. Lubricants produced by the process cover the full range of lubricant viscosities and exhibit a remarkably high VI and low pour point even at high viscosity. Products of higher viscosity can also be produced by operating the oligomerization process at lower temperatures, typically $-20°$ to $+90°$ C., and these high viscosity products are useful as lubricant additives, especially VI improvers for both mineral and synthetic oils, as described in copending application Ser. No. 07/345,606, filed May 1, 1989, now U.S. Pat. No. 5,012,020, to which reference is made for a description of these higher viscosity oligomers, their properties and uses and of the method by which they may be made.

The process for preparing the HVI-PAO lubricants comprises, as noted above, contacting a $C_{6-20}$ 1-alkene feedstock with reduced valence state metal, preferably chromium, oxide catalyst on a porous support such as amorphous silica. The reaction is carried out under oligomerizing conditions in an oligomerization zone to produce a high viscosity, high VI liquid hydrocarbon lubricant with branch ratios less than 0.19 and pour points typically below $-15°$ C. Carbon numbers for the oligomer products typically range from about $C_{30}$ to about $C_{10,000}$, with a preferred range from about $C_{30}$ to about $C_{5,000}$. The oligomerization temperature is typically maintained at a value between 90° and 250° C. to produce the products of typical lubricant viscosity but if the oligomerization process is operated at lower temperatures, higher viscosity materials may be produced; these materials may be used as viscosity index (VI) improvers for lubricants, both of mineral oil and synthetic origin, as described Ser. No. 07/345,606. The higher viscosity HVI-PAO products typically have viscosities between 725 and 15,000 cS at 100° C., corresponding to weight molecular weights from about 15,000 to 200,000 and number molecular weights from about 5,000 to about 50,000. Like the liquid lubricant oligomers, the higher molecular weight oligomers are characterized by high VI coupled with excellent low temperature fluidity properties including pour point for the liquid products.

Summary of the Invention

We have now found that a new class of materials—the crystalline mesoporous solids—are highly suitable support materials for preparing the catalysts used to make the HVI-PAO olefin oligomers. The catalysts made with the mesoporous solid supports enable oligomers with viscosities significantly greater than those produced with the more conventional type of support such as amorphous silica. This enables lubricant oligomers with differing properties to be produced, extending the potential range of lubricant products.

When the oligomer products are made with catalysts using amorphous supports, for example, reduced chromium on silica, control of product viscosity was determined largely by reaction temperature, as described above with decreasing product viscosity at increasing temperatures. The use of the catalysts made with the crystalline mesoporous support materials enables products of widely differing viscosity to be made without resort to change of reaction temperature for the oligomerization. In this way, flexibility of operation is improved and product characteristics may be modified over a wider range.

The support material is a mesoporous solid material which comprises an inorganic, porous non-layered crystalline phase exhibiting, after calcination, an X-ray diffraction pattern with at least one d-spacing greater than about 18 Å and having a benzene adsorption capacity of greater than 15 grams benzene per 100 grams of the material at 50 torr and 25° C. The crystalline material has, in its preferred catalytic form, referred to here as MCM-41, a hexagonal arrangement of uniformly-sized pores having diameters of at least about 13 Å. This material exhibits a hexagonal electron diffraction pattern that can be indexed with a $d_{100}$ value greater than about 18 Å. In addition, at least one peak of the X-ray diffraction pattern has a d-spacing corresponding to the $d_{100}$ value from the electron diffraction pattern. The support materials are described in greater detail in U.S. Pat. Nos. 5,102,643; 5,098,684 and Application Ser. No. 07/734,825, filed Jul. 24 1991, to which reference is made for a complete description of these support materials.

BRIEF DESCRIPTION OF DRAWINGS

In the accompanying drawings.

DETAILED DESCRIPTION

Olefin Oligomer

Figure 1:
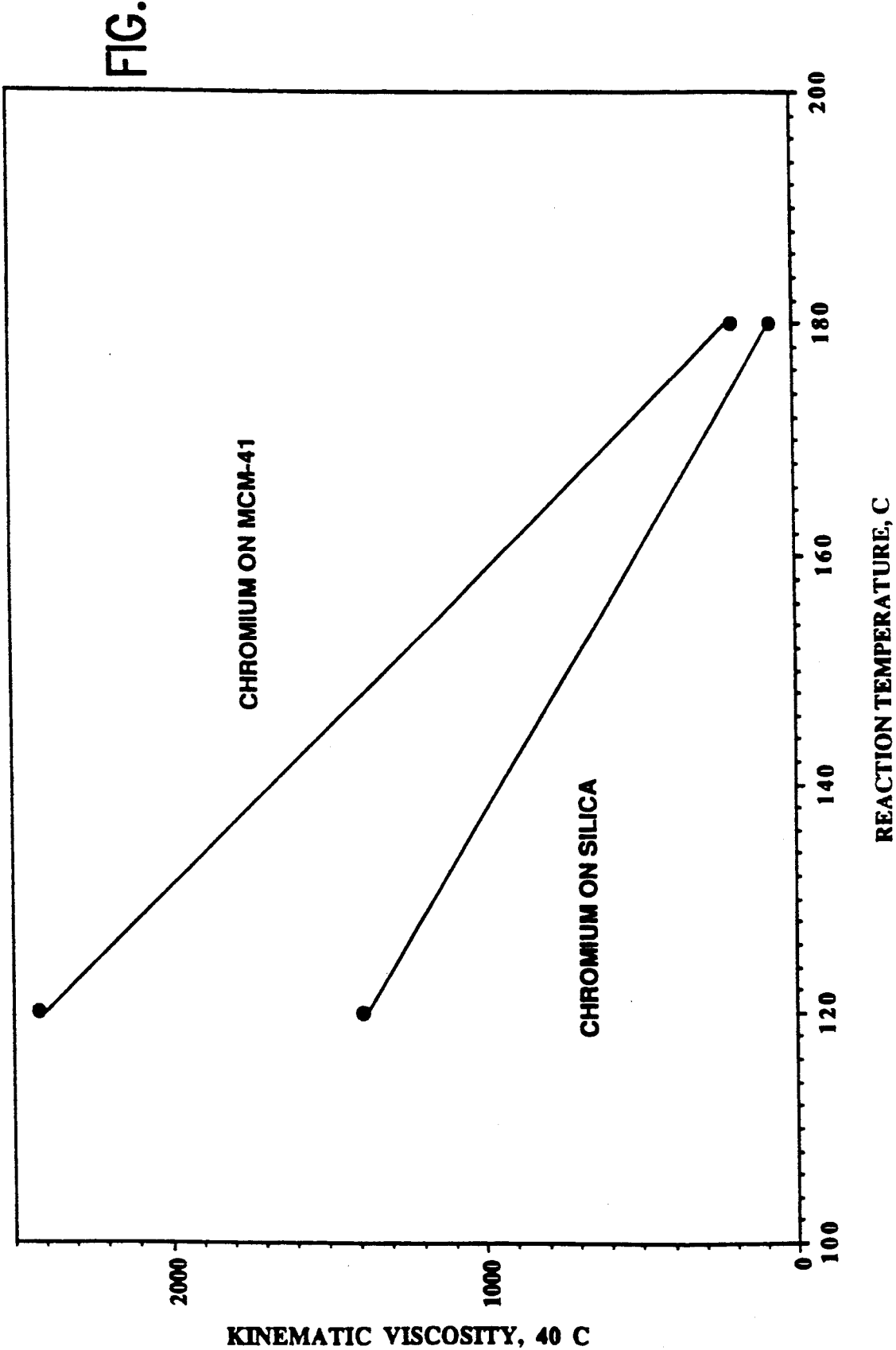
FIGS. 1 and 2 are graphical plots of the relationship between oligomerization temperature and the kinematic viscosities of the oligomer products obtained with catalysts having different support materials.

The olefin oligomers are produced from the oligomerization of 1-alkenes over a reduced metal oxide catalyst, usually reduced chromium oxide. The metal component of the catalyst, e.g. reduced chromium oxide, is supported on a novel type of solid, porous material which is described in detail below. As oligomerized, the HVI-PAO oligomers obtained from the process resemble the HVI-PAO oligomers produced with chromium/silica catalysts, being mixtures of dialkyl vinylidenic and 1,2 dialkyl or trialkyl mono-olefin oligomers. Oligomerization of the olefin feed with the reduced metal oxide catalysts leads to an oligomer which is substantially free of double bond isomerization and has a high degree of linearity. Conventional PAO, on the other hand, formed by oligomerization over Lewis acid catalysts such as $BF_3$ or $AlCl_3$, are formed by a carbonium ion which, in turn, promotes isomerization of the olefinic bond and the formation of multiple isomers of lower linearity, as shown by their branch ratios of above 0.19, as compared to the lower ratios characteristic of the HVI-PAO materials.

Olefins suitable for use as starting material in the preparation of olefinic HVI-PAO oligomers useful as starting material in the present invention include those olefins containing from 2 to about 20 carbon atoms such as ethylene, propylene, 1-butene, 1-pentene, 1-hexene, 1-octene, 1-decene, 1-dodecene and 1-tetradecene and branched chain isomers such as 4-methyl-1-pentene. Also suitable for use are olefin-containing refinery feedstocks or effluents. However, the olefins used in this invention are preferably alpha olefinic as for example 1-hexene to 1-hexadecene and more preferably 1-octene to 1-tetradecene, or mixtures of such olefins.

In the oligomerization process, the olefin feed is contacted with the oligomerization catalyst to produce the desired oligomer product. An alpha-olefin feedstock comprising olefins of 6 to 20 carbon atoms, or mixtures of such olefins, is contacted with the oligomerization catalyst under oligomerization conditions, suitably at a reaction temperature between −20° to 250° C. Temperatures from about 90° to 250° C. produce the lower viscosity oligomer products while lower temperatures, typically in the range of −20° to +90° C. produce the higher viscosity products. Thus, the viscosity of the oligomer product will dependent upon the temperature used in the oligomerization process, as with the silica-supported catalysts.

Oligomerization Catalyst

The catalyst comprises a reduced metal oxide on a porous, solid support. The metal oxide is derived from a metal of Group VIB, preferably chromium, as the catalytic component on a porous support. The catalyst may be activated by treatment including oxidation at a temperature of 200° C. to 900° C. in the presence of an oxidizing gas and then by treatment with a reducing agent, preferably carbon monoxide, at a temperature and for a time sufficient to reduce the metal to a lower valence state. The catalyst most preferred is a lower valence Group VIB metal oxide on the porous support.

The high surface area mesoporous support is beneficial for supporting large amount of highly dispersive, active chromium metal centers and to give maximum efficiency of metal usage, resulting in very high activity catalyst. catalyst may be used in fixed bed or slurry reactor and may be recycled and regenerated.

The supported metal oxide catalysts are preferably prepared by impregnating metal salts in water or organic solvents onto the support. Any suitable organic solvent may be used, for example, ethanol, methanol, or acetic acid. The solid catalyst precursor is then dried and calcined at 200° to 900° C. air or other oxygen-containing gas. The catalyst is then reduced by a reducing agent such as, for example, CO, $H_2$, $NH_3$, $H_2S$, $CS_2$, $CH_3SCH_3$, $CH_3SSCH_3$, metal alkyl containing compounds such as $R_3Al$, $R_3B$, $R_2Mg$, RLi, $R_2Zn$, where R is alkyl, alkoxy, aryl and the like. Preferred are CO or $H_2$ or metal alkyl containing compounds. Alternatively, the Group VI metal may be applied to the substrate in reduced form, such as CrII compounds. The resultant catalyst is very active for oligomerizing olefins at a temperature range from below room temperature to about 250° C. at a pressure of 0.1 atmosphere to 5000 psi. Contact time of both the olefin and the catalyst can vary from one second to 24 hours. The catalyst can be used in a batch type reactor or in a fixed bed, continuous-flow reactor.

The support material may usually be added to a solution of the metal compounds, e.g., acetates or nitrates, etc., and the mixture is then mixed and dried at room temperature. The dry solid gel is purged with air at successively higher temperatures to about 600° for a period of about 16 to 20 hours. After this, the catalyst is cooled down under an inert atmosphere to a temperature of about 250° to 450° C. and a stream of reducing agent such as CO or $H_2$ is contacted with the catalyst for a period to reduce the catalyst as indicated by a distinct color change from bright orange to bluish green. Typically, the catalyst is treated with an amount of CO equivalent to a two-fold stoichiometric excess to reduce the catalyst to a lower valence Cr(II) state. Finally the catalyst is cooled down to room temperature and is ready for use.

Further descriptions of the metal component of the catalyst are given in U.S. Pat. Nos. 4,482,064 and 4,482,073.

Catalyst Support

The catalyst support used in the present oligomerization process is a mesoporous solid. Recent developments in catalyst technology have provided a group of mesoporous siliceous materials having novel pore geometry which are used as the support for the reduced metal oxide component of the oligomerization catalyst. The mesoporous crystalline materials are described in detail in U.S. Pat. No. 5,102,643 and 5,098,684 ans Ser. No. 07/734,825, to which reference is made for a complete description of them.

The mesoporous support material comprises an inorganic, porous non-layered crystalline phase exhibiting, after calcination, an X-ray diffraction pattern with at least one d-spacing greater than about 18 Å and having a benzene adsorption capacity of greater than 15 grams benzene per 100 grams of the material at 50 torr and 25° C. The preferred support, referred to here as MCM-41, is characterized by a hexagonal arrangement of uniformly-sized pores having diameters of at least about 13 Å, preferably in the mesoporous range of about 20–100 Å. This material exhibits a hexagonal electron diffraction pattern that can be indexed with a $d_{100}$ value greater than about 18 Å. In addition, at least one peak of the X-ray diffraction pattern has a d-spacing corresponding to the d100 value from the electron diffraction pattern.

These support materials are crystalline i.e. have sufficient order to provide a diffraction pattern such as, for example, by X-ray, electron or neutron diffraction, following calcination, with at least one peak. They may be characterized as mesoporous materials with a structure including extremely large pore windows, and a high sorption capacity. The term "mesoporous" is used here to indicate crystals having uniform pores within the range of from about 13 Å to about 200 Å, more usually 18 or 20 to 100 Å. For the purposes of this application, a working definition of "porous" is a material that adsorbs at least 1 gram of a small molecule, such as Ar, $N_2$, n-hexane or cyclohexane, per 100 grams of the solid. Since these materials may possess pores with sizes significantly larger than those of previously known crystalline phases, it is also appropriate to regard them as ultra-large pore size materials.

The inorganic, non-layered mesoporous crystalline catalytic material employed as the support materials has the following composition:

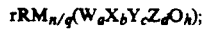

wherein W is a divalent element, such as a divalent first row transition metal, e.g. manganese, cobalt and iron, and/or magnesium, preferably cobalt; X is a trivalent element, such as aluminum, boron, iron and/or gallium, preferably aluminum; Y is a tetravalent element such as silicon and/or germanium, preferably silicon; Z is a pentavalent element, such as phosphorus; M is one or more ions, such as, for example, ammonium, Group IA, IIA and VIIB ions, usually hydrogen, sodium and/or fluoride ions; n is the charge of the composition excluding M expressed as oxides; q is the weighted molar average valence of M; n/q is the number of moles or mole fraction of M; a, b, c, and d are mole fractions of W, X, Y and Z, respectively; h is a number of from 1 to 2.5; and $(a+b+c+d)=1$.

A preferred embodiment of the above crystalline material is when $(a+b+c)$ is greater than d, and $h=2$. A further embodiment is when a and $d=0$, and $h=2$, i.e. an aluminosilicate. The preferred support materials include the ultra-large pore crystalline aluminosilicates having a silica-to-alumina ratio of about 5:1 to 1000:1.

In the as-synthesized form, the support material has a composition, on an anhydrous basis, expressed empirically as follows:

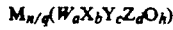

wherein R is the total organic material not included in M as an ion, and r is the coefficient for R, i.e. the number of moles or mole fraction of R.

The M and R components are associated with the material as a result of their presence during crystallization, and are easily removed or, in the case of M, replaced by post-crystallization methods hereinafter more particularly described. To the extent desired, the original M cations, e.g. sodium or chloride, ions of the as-synthesized material of this invention can be replaced in accordance with techniques well known in the art, at least in part, by ion exchange with other ions. Preferred replacing ions include metal ions, hydrogen ions, hydrogen precursor, e.g. ammonium, ions and mixtures of ions, such as hydrogen, and metal cations.

The preferred forms of the support materials used for the present oligomerization catalysts can be distinguished from other porous inorganic solids by the regularity of the large open pores, whose pore size more nearly resembles that of amorphous or paracrystalline materials, but whose regular arrangement and uniformity of size (pore size distribution within a single phase of, for example, ±25%, usually ±15% or less of the average pore size of that phase) resemble more those of crystalline framework materials such as zeolites. The internal diameters of the open pores typically vary from about 13 Å to about 200 Å. The term "hexagonal" is intended to encompass not only materials that exhibit mathematically perfect hexagonal symmetry within the limits of experimental measurement, but also those with significant observable deviations from that ideal state. A working definition as applied to the microstructure of the present invention would be that most channels in the material would be surrounded by six nearest neighbor channels at roughly the same distance. Defects and imperfections will cause significant numbers of channels to violate this criterion to varying degrees, depending on the quality of the material's preparation. Samples which exhibit as much as ±25% random deviation from the average repeat distance between adjacent channels still clearly give recognizable images of the present ultra-large pore materials. Comparable variations are also observed in the $d_{100}$ values from the electron diffraction patterns.

The most regular preparations of the material of the present invention give an X-ray diffraction pattern with a few distinct maxima in the extreme low angle region. The positions of these peaks approximately fit the positions of the hk0 reflections from a hexagonal lattice. The X-ray diffraction pattern, however, is not always a sufficient indicator of the presence of these materials, as the degree of regularity in the microstructure and the extent of repetition of the structure within individual particles affect the number of peaks that will be observed. Indeed, preparations with only one distinct peak in the low angle region of the X-ray diffraction pattern have been found to contain substantial amounts of the material in them. Other techniques to illustrate the microstructure of this material are transmission electron microscopy and electron diffraction. Properly oriented specimens of the material show a hexagonal arrangement of large channels and the corresponding electron diffraction pattern gives an approximately hexagonal arrangement of diffraction maxima. The $d_{100}$ spacing of the electron diffraction patterns is the distance between adjacent spots on the hk0 projection of the hexagonal lattice and is related to the repeat distance $a_0$ between channels observed in the electron micrographs through the formula $d_{100}=a_0\sqrt{3}/2$. This d100 spacing observed in the electron diffraction patterns corresponds to the d-spacing of a low angle peak in the X-ray diffraction pattern of the material. The most highly ordered preparations of the material obtained so far have 20-40 distinct spots observable in the electron diffraction patterns. These patterns can be indexed with the hexagonal hk0 subset of unique reflections of 100, 110, 200, 210, etc., and their symmetry-related reflections.

In its calcined form, the crystalline support material may be further characterized by an X-ray diffraction pattern with at least one peak at a position greater than about 18 Å d-spacing (4,909° 2 ¶ for Cu K-alpha radiation) which corresponds to the $d_{100}$ value of the electron diffraction pattern of the material, and an equilibrium benzene adsorption capacity of greater than about 15 grams benzene/100 grams crystal at 50 torr and 25° C. (basis: crystal material having been treated in an attempt to insure no pore blockage by incidental contaminants, if necessary).

The equilibrium benzene adsorption capacity characteristic of this material is measured on the basis of no pore blockage by incidental contaminants. For instance, the sorption test will be conducted on the crystalline material phase having any pore blockage contaminants and water removed by ordinary methods. Water may be removed by dehydration techniques, e.g. thermal treatment. Pore blocking inorganic amorphous materials, e.g. silica, an organics may be removed by contact with acid or base or other chemical agents such that the detrital material will be removed without detrimental effect on the crystal of the invention.

The calcined crystalline non-layered support material with the hexagonal structure may be characterized by an X-ray diffraction pattern with at least two peaks at positions greater than about 10 Angstrom Units d-spacing (8.842 degrees two-theta for Cu K-alpha radiation), at least one of which is at a position greater than about 18 Angstrom Units d-spacing, and no peaks at positions less than about 10 Å d-spacing with relative intensity greater than about 20% of the strongest peak. More particularly, the X-ray diffraction pattern of the calcined material will have no peaks at positions less than about 10 Å d-spacing with relative intensity greater than about 10% of the strongest peak. In any event, at least one peak in the X-ray diffraction pattern will have a d-spacing that corresponds to the $d_{100}$ value of electron diffraction pattern of the material.

The calcined inorganic, non-layered crystalline support material is also characterized as having a pore size of about 13 Å or greater as measured by physisorption measurements, set out below. Pore size is considered a maximum perpendicular cross-section pore dimension of the crystal.

X-ray diffraction data were collected on a Scintag PAD X automated diffraction system employing theta-theta geometry, Cu K-alpha radiation, and an energy dispersive X-ray detector. Use of the energy dispersive X-ray detector eliminated the need for incident or diffracted beam monochromators. Both the incident and diffracted X-ray beams were collimated by double slit incident and diffracted collimation systems. The slit sizes used, starting from the X-ray tube source, were 0.5, 1.0, 0.3 and 0.2 mm, respectively. Different slit systems may produce differing intensities for the peaks. The materials of the present invention that have the largest pore sizes may require more highly collimated incident X-ray beams in order to resolve the low angle peak from the transmitted incident X-ray beam.

The diffraction data were recorded by step-scanning at 0.04 degrees of two-theta, where theta is the Bragg angle, and a counting time of 10 seconds for each step. The interplanar spacings, d's, were calculated in Å, and the relative intensities of the lines, $I/I_o$, where $I_o$ is one-hundredth of the intensity of the strongest line, above background, were derived with the use of a profile fitting routine. The intensities were uncorrected for Lorentz and polarization effects. The relative intensities are given in terms of the symbols vs=very strong (75-100), s=strong (50-74), m=medium (25-49) and w=weak (0-24). It should be understood that diffraction data listed as single lines may consist of multiple overlapping lines which under certain conditions, such as very high experimental resolution or crystallographic changes, may appear as resolved or partially resolved lines. Typically, crystallographic changes can include minor changes in unit cell parameters and/or a change in crystal symmetry, without a substantial change in structure. These minor effects, including changes in relative intensities, can also occur as a result of differences in cation content, framework composition, nature and degree of pore filling, thermal and/or hydrothermal history, and peak width/shape variations due to particle size/shape effects, structural disorder or other factors known to those skilled in the art of X-ray diffraction.

The equilibrium benzene adsorption capacity is determined by contacting the material of the invention, after dehydration or calcination at, for example, about 540° C. for at least about one hour and other treatment, if necessary, in an attempt to remove any pore blocking contaminants, at 25° C. and 50 torr benzene until equilibrium is reached. The weight of benzene sorbed is then determined as more particularly described hereinafter.

The crystalline support material, especially in its metal, hydrogen and ammonium forms can be beneficially converted to another form by thermal treatment (calcination). This thermal treatment is generally performed by heating one of these forms at a temperature of at least 400° C. for at least 1 minute and generally not longer than 20 hours, preferably from about 1 to about 10 hours, usually at a temperature up to about 750° C.

The crystalline support material should be dehydrated prior to deposition of the chromium component, at least partially. This can be done by heating to a temperature in the range of 200° C. to 595° C. in an atmosphere such as air nitrogen, etc. and at atmospheric, subatmospheric or superatmospheric pressures for between 30 minutes and 48 hours. Dehydration can also be performed at room temperature merely by placing the composition in a vacuum, but a longer time is required to obtain a sufficient amount of dehydration.

Among the ultra-large pore size materials is a new metallosilicate called MCM-41, which is usually synthesized with Bronsted acid active sites by incorporating a tetrahedrally coordinated trivalent element, such as Al, Ga, B, or Fe, within the silicate framework. Aluminosilicate materials of this type are thermally and chemically stable, properties favored for acid catalysis; however, the advantages of mesoporous structures may be utilized by employing highly siliceous materials or crystalline metallosilicate having one or more tetrahedral species having varying degrees of acidity. In addition to the preferred aluminosilicates, the gallosilicate, ferrosilicate and borosilicate materials may be employed. Although matrices may be formed with the germanium analog of silicon, these are expensive and generally no better than the metallosilicates.

The hexagonal MCM-41 crystalline structure is readily recognized by its spectrographic characteristics, such as electron micrograph, X-ray diffraction pattern, absorbtion properties, etc., as described in U.S. Pat. No. 5,098,684, to which reference is made for a detailed description of this material.

Another group of crystalline materials within the class of mesoporous crystalline materials is the group described in U.S. patent application Ser. No. 07/734,825, filed Jul. 24, 1991, to which reference is made for a detailed description of these materials, their preparation and properties. The members of this class of materials can be distinguished by the characteristic X-ray diffraction pattern of the calcined material. Using $d_1$ to indicate the d-spacings of the strongest peak in the X-ray diffraction pattern (relative intensity = 100), the X-ray diffraction pattern of the calcined material exhibits $d_1$ at a position greater than about 18 Angstroms d-spacing and at least one additional weaker peak with d-spacing $d_2$ such that the ratios of these d-spacings relative to $d_1$ (i.e. $d_n/d_1$) correspond to the ranges given in Table 1.

TABLE 1

| d-Spacing $d_n$, Angstroms | $d_n/d_1$ | Relative Intensity |
|---|---|---|
| $d_1$, ≥ ~18 | 1.0 | 100 |
| $d_2$ | 0.87 ± 0.06 | w-m |

More particularly, the X-ray diffraction pattern of the calcined material includes at least two additional weaker peaks at d-spacings $d_2$ and $d_3$ such that the ratios of these d-spacings relative to the strongest peak $d_1$ (at a position greater than about 18 Angstroms d-spacing) correspond to the ranges given in Table 2.

TABLE 2

| d-Spacing $d_n$, Angstroms | $d_n/d_1$ | Relative Intensity |
|---|---|---|
| $d_1$, ≥ ~18 | 1.0 | 100 |
| $d_2$ | 0.87 ± 0.06 | w-m |
| $d_3$ | 0.52 ± 0.04 | w |

Still more particularly, the X-ray diffraction pattern of the calcined materials includes at least four additional weaker peaks at d-spacings $d_2$, $d_3$, $d_4$ and $d_5$ such that the ratios of these d-spacings relative to the strongest peak $d_1$ (at a position greater than about 18 Angstroms d-spacing) correspond to the ranges given in Table 3.

TABLE 3

| d-Spacing $d_n$, Angstroms | $d_n/d_1$ | Relative Intensity |
|---|---|---|
| $d_1$, ≥ ~18 | 1.0 | 100 |
| $d_2$ | 0.87 ± 0.06 | w-m |

TABLE 3-continued

| d-Spacing $d_n$, Angstroms | $d_n/d_1$ | Relative Intensity |
|---|---|---|
| $d_3$ | 0.55 ± 0.02 | w |
| $d_4$ | 0.52 ± 0.01 | w |
| $d_5$ | 0.50 ± 0.01 | w |

Specific examples of calcined materials of this group exhibit an X-ray diffraction pattern including at least two peaks at positions corresponding to the ranges given in Table 4.

TABLE 4

| d-Spacing, Angstroms | Relative Intensity |
|---|---|
| 33.0 ± 2.0 | 100 |
| 28.7 ± 1.5 | w |

More particularly, the X-ray diffraction patterns of the calcined examples presented herein can be characterized as including at least three peaks at positions corresponding to the ranges given in Table 5.

TABLE 5

| d-Spacing, Angstroms | Relative Intensity |
|---|---|
| 33.0 ± 2.0 | 100 |
| 28.7 ± 1.5 | w |
| 17.2 ± 1.2 | w |

Still more particularly, the X-ray diffraction patterns of some calcined examples presented herein can be characterized as including at least five peaks at positions corresponding to the ranges given in Table 6.

TABLE 6

| d-Spacing, Angstroms | Relative Intensity |
|---|---|
| 33.0 ± 2.0 | 100 |
| 28.7 ± 1.5 | w |
| 18.2 ± 0.5 | w |
| 17.2 ± 0.4 | w |
| 16.5 ± 0.3 | w |

In discussing tetrahedrally coordinated metal oxides of the zeolitic type, adjacent metal sites in the matrix are linked by oxygen (i.e., —Si—O—Si—). The honeycomb microstructure of MCM-41 and related mesoporous materials may include several moieties interconnected in a three dimensional matrix or lattice having large hexagonal channels forming the ultra large pores of the catalyst. The repeating units forming the large ring structure of the lattice vary with pore size. A typical support component consists essentially of crystalline aluminosilicate having the structure of MCM-41, optionally containing 5 to 95 wt. % silica, clay and/or alumina binder.

The crystalline support material can be prepared by one of several methods, each with particular limitations.

A first method involves a reaction mixture having an $X_2O_3/YO_2$ mole ratio of from 0 to about 0.5, but an $Al_2O_3/SiO_2$ mole ratio of from 0 to 0.01, a crystallization temperature of from about 25° C. to about 250° C., preferably from about 50° C. to about 175° C., and an organic directing agent, hereinafter more particularly described, or, preferably a combination of that organic directing agent plus an additional organic directing agent, described below. This first method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, an organic (R) directing agent, hereinafter more particularly described, and a solvent or solvent mixture, such as, for example, $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $X_2O_3$/$YO_2$ | 0 to 0.5 | 0.001 to 0.5 |
| $Al_2O_3$/$SiO_2$ | 0 to 0.01 | 0.001 to 0.01 |
| $X_2O_3$/($YO_2$ + $Z_2O_5$) | 0.1 to 100 | 0.1 to 20 |
| $X_2O_3$/($YO_2$ + WO + $Z_2O_5$) | 0.1 to 100 | 0.1 to 20 |
| Solvent/ ($YO_2$ + WO + $Z_2O_5$ + $X_2O_3$) | 1 to 1500 | 5 to 1000 |
| $OH^-$/$YO_2$ | 0 to 10 | 0 to 5 |
| ($M_{2/e}O$ + $R_{2/f}O$)/ ($YO_2$ + WO + $Z_2O_5$ + $X_2O_3$) | 0.01 to 20 | 0.05 to 5 |
| $M_{2/e}O$/ ($YO_2$ + WO + $Z_2O_5$ + $X_2O_3$) | 0 to 10 | 0 to 5 |
| $R_{2/f}O$/ ($YO_2$ + WO + $Z_2O_5$ + $X_2O_3$) | 0.01 to 2.0 | 0.03 to 1.0 | where e and f are the weighted average valences of M and R, respectively.

In this first method, when no Z and/or W oxides are added to the reaction mixture, the pH is important and must be maintained at from about 9 to about 14. When Z and/or W oxides are present in the reaction mixture, the pH is not narrowly important for synthesis of the present crystalline material. In this, as well as the following methods for synthesis of the present material the $R_{2/f}O$/($YO_2$+WO+$Z_2O_5$+$X_2O_3$) ratio is important. When this ratio is less than 0.01 or greater than 2.0, impurity products tend to be synthesized at the expense of the present material.

A second method for synthesis of the crystalline material involves a reaction mixture having an $X_2O_3$/$YO_2$ mole ratio of from about 0 to about 0.5, a crystallization temperature of from about 25° C. to about 250° C., preferably from about 50° C. to about 175° C., and two separate organic directing agents, i.e. the organic and additional organic directing agents, described below. This second method comprises preparing a reaction mixture containing sources of, for example, alkali or alkaline earth metal (M), e.g. sodium or potassium, cation if desired, one or a combination of oxides selected from the group consisting of divalent element W, e.g. cobalt, trivalent element X, e.g. aluminum, tetravalent element Y, e.g. silicon, and pentavalent element Z, e.g. phosphorus, a combination of organic directing agent and additional organic directing agent (R), as described, and a solvent or solvent mixture, such as, for example, $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $X_2O_3$/$YO_2$ | 0 to 0.5 | 0.001 to 0.5 |
| $X_2O_3$/($YO_2$ + $Z_2O_5$) | 0.1 to 100 | 0.1 to 20 |
| $X_2O_3$/($YO_2$ + WO + $Z_2O_5$) | 0.1 to 100 | 0.1 to 20 |
| Solvent/ ($YO_2$ + WO + $Z_2O_5$ + $X_2O_3$) | 1 to 1500 | 5 to 1000 |
| $OH^-$/$YO_2$ | 0 to 10 | 0 to 5 |
| ($M_{2/e}O$ + $R_{2/f}O$)/ ($YO_2$ + WO + $Z_2O_5$ + $X_2O_3$) | 0.01 to 20 | 0.05 to 5 |
| $M_{2/e}O$/ ($YO_2$ + WO + $Z_2O_5$ + $X_2O_3$) | 0 to 10 | 0 to 5 |
| $R_{w/f}O$/ ($YO_2$ + WO + $Z_2O_5$ + $X_2O_3$) | 0.1 to 2.0 | 0.12 to 1.0 | where e and f are the weighted average valences of M and R, respectively.

In this second method, when no Z and/or W oxides are added to the reaction mixture, the pH is important and must be maintained at from about 9 to about 14. When Z and/or W oxides are present in the reaction mixture, the pH is no important for crystallization.

A third method for synthesis of the crystalline material is where X comprises aluminum and Y comprises silicon, the crystallization temperature must be from about 25° C. to about 175° C., preferably from about 50° C. to about 150° C., and an organic directing agent, described below, or, preferably a combination of that organic directing agent plus an additional organic agent, described below, is used. This third method comprises preparing a reaction mixture containing sources of, for example, alkali or alkaline earth metal (M),e.g. sodium or potassium, cation if desired, one or more sources of aluminum and/or silicon, an organic (R) directing agent, described below, and a solvent or solvent mixture such as, for example $C_1$–$C_6$ alcohols, $C_1$–$C_6$ diols and/or water, especially water. The reaction mixture has a composition, in terms of mole ratios of oxides, within the following ranges:

| Reactants | Useful | Preferred |
|---|---|---|
| $Al_2O_3$/$SiO_2$ | 0 to 0.5 | 0.001 to 0.5 |
| Solvent/$SiO_2$ | 1 to 1500 | 5 to 1000 |
| $OH^-$/$SiO_2$ | 0 to 10 | 0 to 5 |
| ($M_{2/e}O$ + $R_{w/f}O$)/ ($SiO_2$ + $Al_2O_3$) | 0.01 to 20 | 0.05 to 5 |
| $M_{2/e}O$/ ($SiO_2$ + $Al_2O_3$) | 0 to 5 | 0 to 3 |
| $R_{w/f}O$/ ($SiO_2$ + $Al_2O_3$) | 0.01 to 2 | 0.03 to 1 | where e and f are the weighted average valences of M and R, respectively.

In this third method, the pH is important and must be maintained at from about 9 to about 14. This method involves the following steps:

(1) Mix the organic (R) directing agent with the solvent or solvent mixture such that the mole ratio of solvent/$R_{2/f}O$ is within the range of from about 50 to about 800, preferably from about 50 to 500. This mixture constitutes the "primary template" for the synthesis method.

(2) To the primary template mixture of step (1) add the sources of oxides, e.g. silica and/or alumina such that the ratio of $R_{2/f}O$/($SiO_2$+$Al_2O_3$) is within the range of from about 0.01 to about 2.0.

(3) Agitate the mixture resulting from step (2) at a temperature of from about 20° C. to about 40° C., preferably for from about 5 minutes to about 3 hours.

(4) Allow the mixture to stand with or without agitation, preferably at a temperature of from about 20° C. to about 100° C., and preferably for from about 10 minutes to about 24 hours.

(5) Crystallize the product from step (4) at a temperature of from about 50° C. to about 175° C., preferably for from about 1 hour to about 72 hours. Crystallization temperatures higher in the given ranges are most preferred.

A fourth method for the synthesis involves the reaction mixture used for the third method, but the following specific procedure with tetraethylorthosilicate the source of silicon oxide:

(1) Mix the organic (R) directing agent with the solvent or solvent mixture such that the mole ratio of solvent/$R_2/O$ is within the range of from about 50 to about 800, preferably from about 50 to 500. This mixture constitutes the "primary template" for the synthesis method.

(2) Mix the primary template mixture of step (1) with tetraethylorthosilicate and a source of aluminum oxide, if desired, such that the $R_2/O/SiO_2$ mole ratio is in the range of from about 0.5 to about 2.0.

(3) Agitate the mixture resulting from step (2) for from about 10 minutes to about 6 hours, preferably from about 30 minutes to about 2 hours, at a temperature of from about 0° C. to about 25° C., and a pH of less than 12. This step permits hydrolysis/polymerization to take place and the resultant mixture will appear cloudy.

(4) Crystallize the product from step (3) at a temperature of from about 25° C. to about 150° C., preferably from about 95° C. to about 110° C., for from about 4 to about 72 hours, preferably from about 16 to about 48 hours.

In each of the above methods, batch crystallization of the present crystalline material can be carried out under either static or agitated, e.g. stirred, conditions in a suitable reactor vessel, such as for example, polypropylene jars or Teflon ® lined or stainless steel autoclaves. Crystallization may also be conducted continuously in suitable equipment.

The total useful range of temperatures for crystallization is noted above for each method for a time sufficient for crystallization to occur at the temperature used, e.g. from about 5 minutes to about 14 days. Thereafter, the crystals are separated from the liquid and recovered.

When a source of silicon is used in the synthesis method, it is preferred to use at least in part an organic silicate, such as, for example, a quaternary ammonium silicate. Non-limiting examples of such a silicate include tetramethylammonium silicate and tetraethylorthosilicate.

By adjusting conditions of the synthesis reaction for each method, like temperature, pH and time of reaction, etc., within the above limits, embodiments of the present non-layered crystalline material with a desired average pore size may be prepared. In particular, changing the pH, the temperature or the reaction time may promote formation of product crystals with different average pore size.

Non-limiting examples of various combinations of W, X, Y and Z contemplated for the first and second synthesis methods of the present invention include:

| W  | X  | Y  | Z |
|----|----|----|---|
| —  | Al | Si | — |
| —  | Al | —  | P |
| —  | Al | Si | P |
| Co | Al | —  | P |
| Co | Al | Si | P |
| —  | —  | Si | — | including the combinations of W being Mg, or an element selected from the divalent first row transition metals, e.g. Mn, Co and Fe; X being B, Ga or Fe; and Y being Ge.

An organic directing agent for use in each of the above methods for synthesizing the present material from the respective reaction mixtures is an ammonium or phosphonium ion of the formula $R_1R_2R_3R_4Q^+$, i.e.:

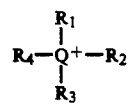

where Q is nitrogen or phosphorus and wherein at least one of $R_1$, $R_2$, $R_3$ and $R_4$ is aryl or alkyl of from 6 to about 36 carbon atoms, e.g. —$C_6H_{13}$, —$C_{10}H_{21}$, —$C_{16}H_{33}$ and —$C_{18}H_{37}$, or combinations thereof, the remainder of $R_1$, $R_2$, $R_3$ and $R_4$ being selected from the group consisting of hydrogen, alkyl of from 1 to 5 carbon atoms and combinations thereof. The compound from which the above ammonium or phosphonium ion is derived may be, for example, the hydroxide, halide, silicate, or mixtures thereof.

In the first and third methods above it is preferred to have an additional organic directing agent and in the second method it is required to have a combination of the above organic directing agent and an additional organic directing agent. That additional organic directing agent is the ammonium or phosphonium ion of the above directing agent formula where $R_1$, $R_2$, $R_3$ and $R_4$ together or separately are selected from the group consisting of hydrogen and alkyl of 1 to 5 carbon atoms and combinations thereof. Any such combination of organic directing agents go to make up "R" and will be in molar ratio of about 100/1 to about 0.01/1, first above listed organic directing agent/additional organic directing agent.

The particular effectiveness of the present directing agents, when compared with other such agents known to direct synthesis of one or more other crystal structures, is believed due to their ability to function as templates in the above reaction mixture in the nucleation and growth of the desired ultra-la pore crystals with the limitations discussed above. Non-limiting examples of these directing agents include cetyltrimethylammonium, cetyltrimethylphosphonium, benzyltrimethylammonium, cetylpyridinium, myristyltrimethylammonium, decyltrimethylammonium, dodecyltrimethylammonium and dimethyldidodecylammonium.

The reaction mixture components can be supplied by more than one source. The reaction mixture can be prepared either batchwise or continuously. Crystal size and crystallization time of the new crystalline material will vary with the nature of the reaction mixture employed and the crystallization conditions.

The crystals prepared by the synthesis procedure can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

Oligomer Product

The product oligomers have atactic molecular structure of mostly uniform head-to-tail connections with some head-to-head type connections in the structure. These low branch ratio oligomers have high viscosity indices at least about 15 to 20 units and typically 30–40 units higher than equivalent viscosity prior art oligomers, which regularly have higher branch ratios and correspondingly lower viscosity indices in the lubricant products. These low branch ratios are also correlated with the lour points of the lubricant products.

The branch ratios are defined as the ratios of $CH_3$ groups to $CH_2$ groups in the oligomers are calculated from the weight fractions of methyl groups obtained by infrared methods, published in *Analytical Chemistry*, Vol. 25, No. 10, p. 1466 (1953).

$$\text{Branch ratio} = \frac{\text{wt. fraction of methyl group}}{1 - (\text{wt fraction of methyl group})}$$

In general the HVI-PAO oligomers have the following regular head-to-tail structure where n is preferably 0 to 17, terminating in olefinic unsaturation:

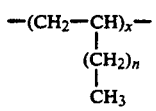

with some head-to-head connections. The as-synthesized HVI-PAO molecular structure generally has one double bond unsaturation.

The HVI-PAO process also produces a different dimer compared to the dimer produced by 1-alkene oligomerization with commercial types of catalyst such as $BF_3$ or $AlCl_3$. Typically, it has been found that a significant proportion of unhydrogenated dimerized 1-alkene has a vinylidenyl structure as follows:

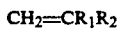

where $R_1$ and $R_2$ are alkyl groups representing the residue from the head-to-tail addition of 1-alkene molecules. For example, 1-decene HVI-PAO dimer, which participates in the post-oligomerization reaction, has been found to contain only three major components, as determined by GC. Based on $C^{13}$ NMR analysis, the unhydrogenated components were found to be 8-eicosene, 9-eicosene, 2-octyldodecene and 9-methyl-8 or 9-methyl-9-nonadecene.

The HVI-PAO oligomers, in the broadest terms, have a weight average molecular weight between 280 and 450,000 and number average molecular weight between 280 and 180,000. Measured in carbon numbers, molecular weights range from $C_{30}$ to $C_{1300}O$ and viscosity up to 7500 cs at 100° C., with a preferred range $C_{30}$ to $C_{1000}$ and a viscosity of up to 1000 cs at 100° C. for lube base stock material. Molecular weight distributions (MWD), defined as the ratio of weight average molecular to number average molecular weight, range from 1.00 to 5, with a preferred range of 1.01 to 3 and a more preferred MWD of about 1.05 to 2.5. The viscosities of the olefinic HVI-PAO oligomers used as alkylating agents in the present process will typically range from 1.5 cS to 7500 cS (measured at 100° C.).

The liquid lubricant compositions produced by the oligomerization process at relatively high oligomerization temperatures e.g. between 90° and 250° C., comprise $C_{30}$–$C_{1300}$ hydrocarbons, with branch ratios of less than 0.19, weight average molecular weights between 300 and 45,000, number average molecular weights between 300 and 18,000. The molecular weight distribution of these oligomers is between 1 and 5 and the pour point of the liquid lubricants is below −15° C.

The viscosity index for the liquid polyalpha-olefins is approximately described by the following equation:

$$VI = 156.8 + 4.94 \times (V_{100°\,C.})^{0.5},$$

where $V_{100°}$ C. is the kinematic viscosity in centistokes measured at 100° C.

Usually, the lubricant range oligomers are produced by varying the oligomerization temperature to yield lubricant viscosity range oligomers having weight average molecular weight between 420 and 45,000 and number average molecular weight between 420 and 18,000. Measured in carbon numbers, molecular weights range from $C_{30}$ to $C_{1300}$ and a viscosity up to 750cs at 100° C., with a preferred range of $C_{30}$ to $C_{1000}$ and a viscosity of up to 500 cS at 100° C. Molecular weight distributions (MWD), defined as the ratio of weight average molecular to number average molecular weight, range from 1.00 to 5, with a preferred range of 1.01 to 3 and a more preferred MWD of about 1.05 to 2.5.° compared to conventional PAO derived from $BF_3$- or $AlCl_3$-catalyzed polymerization of 1-alkene, HVI-PAO has been found to have a higher proportion of higher molecular weight polymer molecules in the product. The viscosities of the lubricant HVI-PAO oligomers (measured at 100° C.) typically range from 3 cS to 5000 cS.; the viscosities obtained with the present catalysts have been found to be greater than those obtained with catalysts using porous support materials.

The higher viscosity oligomers produced at lower oligomerization temperatures e.g. below about 90° C. comprise hydrocarbons which have a branch ratio below 0.19 and a viscosity at 100° C. which is typically from 100 to 20,000 cS. hydrocarbons typically have weight average molecular weights from 15,000 to 200,000 and number average molecular weights from 5,000 to 50,000 with a molecular weight distribution from about 1 to about 5. The viscosity index of the liquid compositions of this type is at least 130 and usually higher, for example, above 180 or even 200 or higher. The high viscosity materials are characterized by high shear stability, being stable under high temperature, high shear rate conditions, notably at 150° C. and a shear rate of one million ($10^6$) reciprocal seconds. Reference is made to Ser. No. 07/345,606 for a more detailed description of these oligomers, their properties and uses as well of the methods by which they may be made.

As oligomerized, the HVI-PAO oligomers are mixtures of dialkyl vinylidenic and 1,2 dialkyl or trialkyl mono-olefins and the lower molecular weight unsaturated oligomers are usually hydrogenated to produce the thermally and oxidatively stable lubricants after removal of the non-lube boiling range fraction (dimer and lower) by distillation.

Products

The products of the process are useful as lubricant basestock and as additives for both mineral and synthetic lubricants. The higher molecular weight products are especially useful as multipurpose lubricant additives since they have excellent VI improvement properties which may be combined with other valuable additive characteristics. The introduction of the aromatic moiety into the HVI-PAO increases thermal stability, increases solubilizing power of the product and may add other properties useful in additives such as antiwear properties and VI enhancement. Therefore, as additives, their usefulness is compounded to incorporate in a single additive product the capability to improve a lube basestock thermal stability, VI, solvency and seal swelling power as well as improving antiwear characteristics. They possess the further advantage of great flexibility in the range of viscosity in which they can be prepared so that their additive properties can be used in a viscosity compatible with the viscosity formulation of the lube basestock.

In Examples 1 to 19 below which illustrate the preparation of the support materials, metric units and parts by weight are employed unless otherwise indicated.

EXAMPLE 1

One hundred grams of cetyltrimethylammonium (CTMA) hydroxide solution, prepared by contacting a 29 wt. % N,N,N- trimethyl-1-hexadecanaminium chloride solution with a hydroxide-for-halide exchange resin, was combined with 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a polypropylene bottle, which was kept in a steam box at 95° C. overnight. The mixture had a composition in terms of moles per mole $Al_2O_3$:

2.7 moles $Na_2O$
392 moles $SiO_2$
35.7 moles $(CTMA)_2O$
61.7 moles $(TMA)_2O$
6231 moles $H_2O$ The resulting solid product was recovered by filtration and dried in air at ambient temperature. The product was then calcined at 50° C. for 1 hour in nitrogen, followed by 6 hours in air.

The calcined product proved to have a surface area of 475 $m^2/g$ and the following equilibrium adsorption capacities in grams/100 grams:

| | |
|---|---|
| $H_2O$ | 8.3 |
| Cyclohexane | 22.9 |
| n-Hexane | 18.2 |
| Benzene | 21.5 |

The product of this example may be characterized by X-ray diffractiion as including a very strong relative intensity line at 37.8±2.0 Å d-spacing, and weak lines at 21.6±1.0 and 19.2±1.0 Å. Transmission electron microscopy (TEM) produced images of a hexagonal arrangement of uniform pores and hexagonal electron diffraction pattern with a $d_{100}$ value of about 39 Å.

EXAMPLE 2

One hundred grams of cetyltrimethylammonium (CTMA) hydroxide solution prepared as in Example 1 was combined with 100 grams of an aqueous solution of tetramethylammonium (TMA) hydroxide (25%) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. overnight. The mixture had a composition in terms of moles per mole $Al_2O_3$:

2.7 moles $Na_2O$
291 moles $SiO_2$
35.7 moles $(CTMA)_2O$
102 moles $(TMA)_2O$
6120 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 993 $m^2/g$ and the following equilibrium adsorption capacities in grams/100 grams:

| | |
|---|---|
| $H_2O$ | 7.1 |
| Cyclohexane | 47.2 |
| n-Hexane | 36.2 |
| Benzene | 49.5 |

The X-ray diffraction pattern of the calcined product may be characterized as including a very strong relative intensity line at 39.3±2.0 Å d-spacing, and weak lines at 22.2±1.0 and 19.4±1.0 Å. TEM indicated that the product contained the ultra-large pore material.

A portion of the above product was then contacted with 100% steam at 1450° F. for two hours. The surface area of the steamed material was measured to be 440 $m^2/g$, indicating that about 45% was retained following severe steaming.

Another portion of the calcined product of this example was contacted with 100% steam at 1250° F. for two hours. The surface area of this material was measured to be 718 $m^2/g$, indicating that 72% was retained after steaming at these conditions.

EXAMPLE 3

Water, cetyltrimethylammonium hydroxide solution prepared as in Example 1, aluminum sulfate, HiSil and an aqueous solution of tetrapropylammonium (TPA) bromide (35%) were combined to produce a mixture having a composition in terms of moles per mole $Al_2O_3$:

0.65 moles $Na_2O$
65 moles $SiO_2$
8.8 moles $(CTMA)_2O$
1.22 moles $(TPA)_2O$
1336 moles $H_2O$ The resulting mixture was placed in a polypropylene bottle, which was kept in a steam box at 95° C. for 192 hours. The sample was then cooled to room temperature and combined with CTMA hydroxide solution prepared as in Example 1 and TMA hydroxide (25% by weight) in the weight ratio of 3 parts mixture, 1 part CTMA hydroxide and 2 parts TMA hydroxide. The combined mixture was then placed in a polypropylene bottle and kept in a steam box at 95° C. overnight. The combined mixture had a composition in terms of moles per mole $Al_2O_3$:

0.65 moles $Na_2O$
65 moles $SiO_2$
15 moles $(CTMA)_2O$
1.22 moles $(TPA)_2O$
35.6 moles $(TMA)_2O$
2927 moles $H_2O$ The resulting solid product was recovered by filtration and dried in air at ambient temperature. The product was then calcined at 540° C. for 1 hour in nitrogen, followed by 6 hours in air.

The calcined product proved to have a surface area of 1085 m²/g and the following equilibrium adsorption capacities in grams/100 grams:

| | |
|---|---|
| H₂O | 11.5 |
| Cyclohexane | >50 |
| n-Hexane | 39.8 |
| Benzene | 62 |

The X-ray diffraction pattern of the calcined product of this example may be characterized as including a very strong relative intensity line at 38.2±2.0 Å d-spacing, and weak lines at 22.2±1.0 and 19.4±1.0 Å. TEM indicated the product contained the ultra-large pore material.

EXAMPLE 4

Two hundred grams of cetyltrimethylammonium (CTMA) hydroxide solution prepared as in Example 1 was combined with 2 grams of Catapal alumina (alpha-alumina monohydrate, 74% alumina) and 100 grams of an aqueous solution of tetramethylammonium (TMA) silicate (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 48 hours. The mixture had a composition in terms of moles per mole Al₂O₃:

0.23 moles Na₂O
33.2 moles SiO₂
6.1 moles (CTMA)₂O
5.2 moles (TMA)₂O
780 moles H₂O The resulting solid product was recovered by filtration and dried in air at ambient temperature. The product was then calcined at 540° C. for 1 hour in nitrogen, followed by 6 hours in air.

The calcined product proved to have a surface area of 1043 m²/g and the following equilibrium adsorption capacities in grams/100 grams:

| | |
|---|---|
| H₂O | 6.3 |
| Cyclohexane | >50 |
| n-Hexane | 49.1 |
| Benzene | 66.7 |

The X-ray diffraction pattern of the calcined product of this example may be characterized as including a very strong relative intensity line at 40.8±2.0 Å d-spacing, and weak lines at 23.1±1.0 and 20.1±1.0 Å. TEM indicated that the product contained the ultra-large pore material.

EXAMPLE 5

Two-hundred sixty grams of water was combined with 77 grams of phosphoric acid (85%), 46 grams of Catapal alumina (74% alumina), and 24 grams of pyrrolidine (Pyr) with stirring. This first mixture was placed in a stirred autoclave and heated to 150° C. for six days. The material was filtered, washed and air-dried. Fifty grams of this product was slurried with 200 grams of water and 200 grams of cetyltrimethylammonium hydroxide solution prepared as in Example 1. Four hundred grams of an aqueous solution of tetraethylammonium silicate (10% silica) was then added to form a second mixture which was placed in a polypropylene bottle and kept in a steam box at 95° C. overnight. The first mixture had a composition in terms of moles per mole Al₂O₃:

1.0 moles P₂O₅
0.51 moles (Pyr)₂O
47.2 moles H₂O

The resulting solid product was recovered by filtration and dried in air at ambient temperature. The product was then calcined at 540° C. for 1 hour in nitrogen, followed by 6 hours in air.

The calcined product proved to have a surface area of 707 m²/g and the following equilibrium adsorption capacities in grams/100 grams:

| | |
|---|---|
| H₂O | 33.2 |
| Cyclohexane | 19.7 |
| n-Hexane | 20.1 |
| Benzene | 23.3 |

The X-ray diffraction pattern of the calcined product may be characterized as including a very strong relative intensity line at 25.4±1.5 Å d-spacing. TEM indicated the product contained the present ultra-large pore material (see Example 23).

EXAMPLE 6

A solution of 1.35 grams of NaAlO₂ (43.5% Al₂O₃, 30% Na₂O) dissolved in 45.2 grams of water was mixed with 17.3 grams of NaOH, 125.3 grams of colloidal silica (40%, Ludox HS-40) and 42.6 grams of 40% aqueous solution of tetraethylammonium (TEA) hydroxide. After stirring overnight, the mixture was heated for 7 days in a steam box (95° C.). Following filtration, 151 grams of this solution was mixed with 31 grams of cetyltrimethylammonium hydroxide solution prepared as in Example 1 and stored in the steam box at 95° C. for 13 days. The mixture had the following relative molar composition:

0.25 moles Al₂O₃
10 moles Na₂O
36 moles SiO₂
0.95 moles (CTMA)₂O
2.5 moles (TEA)₂O
445 moles H₂O The resulting solid product was recovered by filtration and washed with water and ethanol. The product was then calcined at 540° C. for 1 hour in nitrogen, followed by 6 hours in air.

The calcined product composition included 0.14 wt. % Na, 68.5 wt. % SiO₂ and 5.1 wt. % Al₂O₃, and proved to have a benzene equilibrium adsorption capacity of 58.6 grams/100 grams.

The X-ray diffraction pattern of the calcined product may be characterized as including a very strong relative intensity line at 31.4±1.5 Å d-spacing. TEM indicated that the product contained the present ultra-large pore material.

EXAMPLE 7

A mixture of 300 grams of cetyltrimethylammonium (CTMA) hydroxide solution prepared as in Example 1 and 41 grams of colloidal silica (40%, Ludox HS-40) was heated in a 600 cc autoclave at 150° C. for 48 hours with stirring at 200 rpm. The mixture has a composition in terms of moles per mole SiO₂:

0.5 mole (CTMA)₂O 46.5 moles H₂O

The resulting solid product was recovered by filtration, washed with water, then calcined at 540° C. for 1 hour in nitrogen, followed by 10 hours in air.

The calcined product composition included less than 0.01 wt. % Na, about 98.7 wt. % SiO₂ and about 0.01 wt. % Al₂O₃, and proved to have a surface area of 896 m²/g. The calcined product had the following equilibrium adsorption capacities in grams/100 grams:

| | |
|---|---|
| H₂O | 8.4 |
| Cyclohexane | 49.8 |
| n-Hexane | 42.3 |
| Benzene | 55.7 |

The X-ray diffraction pattern of the calcined product of this example may be characterized as including a very strong relative intensity line at 40.0±2.0 Å d-spacing and a weak line at 21.2±1.0 Å. TEM indicated that the product of this example contained at least three separate phases, one of which was the ultra-large pore material.

EXAMPLE 8

A mixture of 150 grams of cetyltrimethylammonium (CTMA) hydroxide solution prepared as in Example 1 and 21 grams of colloidal silica (40%, Ludox HS-40) with an initial pH of 12.64 was heated in a 300 cc autoclave at 150° C. for 48 hours with stirring at 200 rpm. The mixture had a composition in terms of moles per mole SiO₂:

0.5 mole (CTMA)₂O
46.5 moles H₂O

The resulting solid product was recovered by filtration, washed with water, then calcined at 540° C. for 6 hours in air.

The calcined product composition was measured to include 0.01 wt.% Na, 93.2 wt. % SiO₂ and 0.016 wt. % Al₂O₃, and proved to have a surface area of 992 m²/g and the following equilibrium adsorption capacities in grams/100 grams:

| | |
|---|---|
| H₂O | 4.6 |
| Cyclohexane | >50 |
| n-Hexane | >50 |
| Benzene | 62.7 |

The X-ray diffraction pattern of the calcined product may be characterized as including a very strong relative intensity line at 43.6±2.0 A d-spacing and weak lines at 25.1±1.5 and 21.7±1.0 A. TEM indicated that the product contained the ultra-large pore material.

EXAMPLE 9

Sodium aluminate (4.15 g) was added slowly into a solution containing 16 g of myristyltrimethylammonium bromide (C₁₄TMABr) in 100 g of water. Tetramethylammonium silicate (100 g-10% SiO₂), HiSil (25 g) and tetramethylammonium hydroxide (14.2 g-25% solution) were then added to the mixture. The mixture was crystallized in an autoclave at 120° C. with stirring for 24 hours.

The product was filtered, washed and air dried. Elemental analysis showed the product contained 53.3 wt % SiO₂, 3.2 wt % Al₂O₃, 15.0 wt % C, 1.88 wt % N, 0.11 wt % Na and 53.5 wt % ash at 1000° C. The X-ray diffraction pattern of the material after calcination at 540° C. for 1 hour in N₂ and 6 hours in air includes a very strong relative intensity line at 35.3±2.0 Å d-spacing and weak lines at 20.4±1.0 and 17.7±1.0 Å d-spacing. TEM indicated that the product contained the ultra-large pore material.

The washed product, having been exchanged with 1N ammonium nitrate solution at room temperature, then calcined, proved to have a surface area of 827 m²/g and the following equilibrium adsorption capacities in g/100 g anhydrous sorbent:

| | |
|---|---|
| H₂O | 30.8 |
| Cyclohexane | 33.0 |
| n-Hexane | 27.9 |
| Benzene | 40.7 |

EXAMPLE 10

Sodium aluminum (4.15 g) was added slowly into a solution containing 480 g of dodecyltrimethylammonium hydroxide (C₁₂TMAOH, 50%) solution diluted with 120 g of water. UltraSil (50 g) and an aqueous solution of tetramethylammonium silicate (200 g-10% SiO₂) and tetramethylammonium hydroxide (26.38 g-25% solution) were then added to the mixture. The mixture was crystallized in an autoclave at 100° C. with stirring for 24 hours.

The product was filtered, washed and air dried. After calcination at 540° C. for 1 hour in N₂ and 6 hours in air, the X-ray diffraction pattern includes a very strong relative intensity line at 30.4±1.5 Å d-spacing and weak lines at 17.7±1.0 and 15.3±1.0 Å d-spacing. TEM indicated that the product contained the ultra-large pore material.

The washed product, having been exchanged with 1N ammonium nitrate solution at room temperature, then calcined, proved to have a surface area of 1078 m²/g and the following equilibrium adsorption capacities in g/100 g anhydrous sorbent:

| | |
|---|---|
| H₂O | 32.6 |
| Cyclohexane | 38.1 |
| n-Hexane | 33.3 |
| Benzene | 42.9 |

EXAMPLE 11

A solution of 4.9 grams of NaAlO₂ (43.5 % Al₂O₃, 30% Na₂O) in 37.5 grams of water was mixed with 46.3 cc of 40% aqueous tetraethylammonium hydroxide solution and 96 grams of colloidal silica (40%, Ludox HS-40). The gel was stirred vigorously for 0.5 hour, mixed with an equal volume (150 ml) of cetyltrimethylammonium hydroxide solution prepared as in Example 1 and reacted at 100° C. for 168 hours. The mixture had the following composition in terms of moles per mole Al₂O₃:

1.1 moles Na₂O
30.6 moles SiO₂
3.0 moles (TEA)₂O
3.25 moles (CTMA)₂O
609 moles H₂O The resulting solid product was recovered by filtration, washed with water then calcined at 540° C. for 16 hours in air. The calcined product proved to have a surface area of 1352 m²/g and the following equilibrium adsorption capacities in grams/100 grams:

| | |
|---|---|
| H$_2$O | 23.6 |
| Cyclohexane | >50 |
| n-Hexane | 49 |
| Benzene | 67.5 |

The X-ray diffraction pattern of the calcined product may be characterized as including a very strong relative intensity line at 38.5±2.0 Å d-spacing and a weak line at 20.3±1.0 Å. TEM indicated that the product contained the ultra-large pore material.

EXAMPLE 12

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a static autoclave at 150° C. for 24 hours. The mixture had a composition in terms of moles per mole Al$_2$O$_3$:

1.25 moles Na$_2$O
27.8 moles SiO$_2$
5.1 moles (CTMA)$_2$O
4.40 moles (TMA)$_2$O
650 moles H$_2$O The resulting solid product was recovered by filtration and dried in air at ambient temperature. The product was then calcined at 540° C. for 1 hour in nitrogen, followed by 6 hours in air. TEM indicated that this product contained the ultra-large pore material. The X-ray diffraction pattern of the calcined product of this example can be characterized as including a very strong relative intensity line at 44.2±2.0 Å d-spacing and weak lines at 25.2±1.5 and 22.0±1.0Å.

The calcined product proved to have a surface area of 932 m$^2$/g and the following equilibrium adsorption capacities in grams/100 grams:

| | |
|---|---|
| H$_2$O | 39.3 |
| Cyclohexane | 46.6 |
| n-Hexane | 37.5 |
| Benzene | 50 |

EXAMPLE 13

Two hundred grams of cetyltrimethylammonium (CTMA) hydroxide solution prepared as in Example 1 was combined with 4.15 grams of sodium aluminate and 100 grams of aqueous tetramethylammonium (TMA) silicate solution (10% silica) with stirring. Twenty-five grams of HiSil, a precipitated hydrated silica containing about 6 wt. % free water and about 4.5 wt. % bound water of hydration and having an ultimate particle size of about 0.02 micron, was added. The resulting mixture was placed in a steam box at 100° C. for 48 hours. The mixture had a composition in terms of moles per mole Al$_2$O$_3$:

1.25 moles Na$_2$O
27.8 moles SiO$_2$
5.1 moles (CTMA)$_2$O
4.4 moles (TMA)$_2$O
650 moles H$_2$O The resulting solid product was recovered by filtration and dried in air at ambient temperature. The product was then calcined at 540° C. for 1 hour in nitrogen, followed by 6 hours in air. The calcined product proved to have the following equilibrium adsorption capacities in grams/100 grams:

| | |
|---|---|
| H$_2$O | 35.2 |
| Cyclohexane | >50 |
| n-Hexane | 40.8 |
| Benzene | 53.5 |

The X-ray diffraction pattern of the calcined product may be characterized as including a very strong relative intensity line at 39.1±2.0 Å d-spacing and weak lines at 22.4±1.0 and 19.4±1.0 Å. TEM indicated that this product contained the ultra-large pore material.

EXAMPLE 14

A mixture of 125 grams of 29% CTMA chloride aqueous solution, 200 grams of water, 3 grams of sodium aluminate (in 50 grams H$_2$O), 65 grams of Ultrasil, amorphous precipitated silica available from PQ Corporation, and 21 grams NaOH (in 50 grams H$_2$O) was stirred thoroughly and crystallized at 150° C. for 168 hours. The reaction mixture had the following relative molar composition in terms of moles per mole silica:

0.10 moles (CTMA)$_2$O
21.89 moles H$_2$O
0.036 moles NaAlO$_2$
0.53 moles NaOH

The solid product was isolated by filtration, washed with water, dried for 16 hours at room temperature and calcined at 540° C. for 10 hours in air. The calcined product proved to have a surface area of 840 m$^2$/g, and the following equilibrium adsorption capacities in grams/100 grams:

| | |
|---|---|
| H$_2$O | 15.2 |
| Cyclohexane | 42.0 |
| n-Hexane | 26.5 |
| Benzene | 62 |

The X-ray diffraction pattern of the calcined product may be characterized as including a very strong relative intensity line at 40.5±2.0 Å d-spacing. TEM indicated that the product contained the ultra-large pore material.

EXAMPLE 15

To make the primary template mixture for this example, 240 grams of water was added to a 92 gram solution of 50% dodecyltrimethylammonium hydroxide, 36% isopropyl alcohol and 14% water such that the mole ratio of Solvent/R$_2$/O was 155. The mole ratio of H$_2$O/R$_2$/O in this mixture was 149 and the IPA/R$_2$/O mole ratio was 6. To the primary template mixture was added 4.15 grams of sodium aluminate, 25 grams of HiSil, 100 grams of aqueous tetramethylammonium silicate solution (10% SiO$_2$) and 13.2 grams of 25% aqueous tetramethylammonium hydroxide solution. The mole ratio of R$_2$/O/(SiO$_2$+Al$_2$O$_3$) was 0.28 for the mixture.

This mixture was stirred at 25° C. for 1 hour. The resulting mixture was then placed in an autoclave at 100° C. and stirred at 100 rpm for 24 hours. The mixture in the autoclave had the following relative molar composition in terms of moles per mole $SiO_2$:

0.05 mole $Na_2O$
0.036 mole $Al_2O_3$
0.18 mole $(C_{12}TMA)_2O$
0.12 mole $(TMA)_2O$
36.0 moles $H_2O$
1.0 mole IPA The resulting solid product was recovered by filtration, washed with water and dried in air at ambient temperature. The product was then calcined at 540° C. for 1 hour in nitrogen, followed by 6 hours in air.

The calcined product proved to have a surface area of 1223 $m^2/g$ and following equilibrium adsorption capacities in grams/100 grams:

| | |
|---|---|
| $H_2O$ | 25.5 |
| Cyclohexane | 41.1 |
| n-Hexane | 35.1 |
| Benzene | 51 |

The X-ray diffraction pattern of the calcined product may be characterized as including a very strong relative intensity line at 30.8±1.5 Å d-spacing and weak lines at 17.9±1.0 and 15.5±1.0 Å. TEM indicated this product to contain the ultra-large pore material.

EXAMPLE 16

A 50.75 gram quantity of decyltrimethylammonium hydroxide (prepared by contacting a ca. 29 wt. % solution of decyltrimethylammonium bromide with a hydroxide-for-halide exchange resin) was combined with 8.75 grams of tetraethylorthosilicate. The mixture was stirred for about 1 hour and then transferred to a polypropylene jar which was then placed in a steambox for about 24 hours. The mixture had a composition in terms of moles per mole $SiO_2$:

0.81 mole $(C_{10}TMA)_2O$
47.6 moles $H_2O$

The resulting solid product was filtered and washed several times with warm (60°-70° C.) distilled water and with acetone. The final product was calcined to 538° C. in $N_2$/air mixture and then held in air for about 8 hours. The calcined product proved to have a surface area of 915 $m^2/g$ and an equilibrium benzene adsorption capacity of 35 grams/100 grams. Argon physisorption data indicated an argon uptake of 0.34 cc/gram, and a pore size of 15 Å.

The X-ray diffraction pattern of the calcined product of this example may be characterized as including a very strong relative intensity line at 27.5±1.5 Å d-spacing and weak lines at 15.8±1.0 and 13.7±1.0 Å. TEM indicated that the product of this example contained the ultra-large pore material.

EXAMPLE 17

To eighty grams of cetyltrimethylammonium hydroxide (CTMAOH) solution prepared as in Example 1 was added 1.65 grams of $NaAlO_1$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 70 grams of 1,3,5-trimethylbenzene (mesitylene). The resulting mixture was stirred at room temperature for several minutes. The gel was then loaded into a 600 cc autoclave and heated at 105° C. for sixty-eight hours with stirring at 150 rpm. The mixture had a composition in terms of moles per mole $Al_2O_3$:

1.25 moles $Na_2O$
27.8 moles $SiO_2$
5.1 moles $(CTMA)_2O$
2.24 moles $(TMA)_2O$
2256 moles $H_2O$
80.53 moles 1,3,5-trimethylbenzene The resulting product was filtered and washed several times with warm (60°-70° C.) distilled water and with acetone. The final product was calcined to 538° C. in $N_2$/air mixture and then held in air for about 10 hours. The calcined product proved to have an equlibrium benzene adsorption capacity of >25 grams/100 grams.

The X-ray diffraction pattern of the calcined product may be characterized as including a broad, very strong relative intensity line at about 102 Å d-spacing, but accurate positions of lines in the extreme low angle region of the X-ray diffraction pattern are very difficult to determine with conventional X-ray diffractometers. Furthermore, finer collimating slits were required to resolve a peak at this low 2-theta angle. The slits used in this example, starting at the X-ray tube, were 0.1, 0.3, 0.5 and 0.2 mm, respectively. TEM indicated that the product of this example contained several materials with different $d_{100}$ values as observed in their electron diffraction patterns. These materials were found to possess $d_{100}$ values between about 85 Å d-spacing and about 120 Å d-spacing.

EXAMPLE 18

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, 200 grams of water and 120 grams of 1,3,5-trimethylbenzene (mesitylene). The resulting mixture was stirred at room temperature for several minutes. The gel was then loaded into a 600 cc autoclave and heated at 105° C. for ninety hours with stirring at 150 rpm. The mixture had a composition in terms of moles per mole $Al_2O_3$:

1.25 moles $Na_2O$
27.8 moles $SiO_2$
5.1 moles $(CTMA)_2O$
2.24 moles $(TMA)_2O$
2256 moles $H_2O$
132.7 moles 1,3,5-trimethylbenzene The resulting product was filtered and washed several times with warm (60°-70° C.) distilled water and with acetone. The final product was calcined to 538° C. in $N_2$/air mixture and then held in air for about 10 hours. The calcined product proved to have a surface area of 915 $m^2/g$ and an equlibrium benzene adsorption capacity of >25 grams/100 grams. Argon physisorption data indicated an argon uptake of 0.95 cc/gram, and a pore size centered on 78 A (Dollimore-Heal Method, see Example 22(b)), but running from 70 to greater than 105 Angstroms. The X-ray diffraction pattern of the calcined product of this example may be characterized as having only enhanced scattered intensity in the very low angle region of the X-ray diffraction, where intensity from the transmitted incident X-ray beam is usually observed. However, TEM indicated that the product contained several materials with different $d_{100}$ values as observed in their electron diffraction patterns. These materials were found to possess $d_{100}$ values between about 85 Å d-spacing and about 110 Å d-spacing.

EXAMPLE 19

To eighty grams of cetyltrimethylammonium hydroxide (CTMAOH) solution prepared as in Example 1 was added 1.65 grams of $NaAlO_2$. The mixture was stirred at room temperature until the $NaAlO_2$ was dissolved. To this solution was added 40 grams of aqueous tetramethylammonium (TMA) silicate solution (10 wt. % $SiO_2$), 10 grams of HiSil, and 18 grams of 1,3,5-trimethylbenzene (mesitylene). The resulting mixture was stirred at room temperature for several minutes. The gel was then loaded into a 300 cc autoclave and heated at 105° C. for four hours with stirring at 150 rpm. The mixture had a composition in terms of moles per mole $Al_2O_3$:

1.25 moles $Na_2O$
27.8 moles $SiO_2$
5.1 moles $(CTMA)_2O$
2.24 moles $(TMA)_2O$
650 moles $H_2O$
19.9 moles 1,3,5-trimethylbenzene The resulting product was filtered and washed several times with warm (60°–70° C.) distilled water and with acetone. The final product was calcined to 538° C. in $N_2$/air mixture and then held in air for about 8 hours.

The calcined product proved to have a surface area of 975 $m^2/g$ and an equilbrium benzene adsorption capacity of >40 grams/100 grams. Argon physisorption data indicated an argon uptake of 0.97 cc/gram, and a pore size of 63 Å (Dollimore-Heal Method), with the peak occurring at $P/P_o=0.65$.

The X-ray diffraction pattern of the calcined product of this example may be characterized as including a very strong relative intensity line at 63±5 Å d-spacing and weak lines at 36.4±2.0, 31.3±1.5 Å and 23.8±1.0 Å d-spacing. TEM indicated that the product of this example contained ultra-large pore material.

EXAMPLE 20

A catalyst for olefin oligomerization was prepared as follows:

Four hundred grams of cetyltrimethylammonium hydroxide, prepared by contacting a 29 wt % N,N,N-trimethyl-1-hexadecanaminium chloride solution with an excess of hydroxide-to-halide exchange resin, were combined with 200 grams of tetramethylammonium silicate solution (10 wt % silica). Fifty grams of HiSil, a precipitated hydrated silica containing about 6 wt % free water and about 4.5% bound water of hydration and having an ultimate particle size of about 0.02 micron, were then added with stirring. This mixture was place in a polypropylene bottle and put into a steam box for 48 hours. The product was filtered, washed, air-dried, and calcined (1 hour at 540° C. in flowing nitrogen followed by six hours in air). The XRD pattern of this material had a major peak at a d-spacing of approximately 37 Å and was identified as MCM-41.

Three grams of the above material were added to a solution comprised of 0.14 grams of chromium (III) acetate (monohydrate) in 10 cc of water. This mixture was allowed to stir overnight at room temperature. Excess moisture was removed under vacuum.

7 cc (1.85 grams) of the chromium treated catalyst were placed into a fixed-bed reactor. The catalyst was dried in nitrogen at 250° C. for 5 hours. The catalyst was then calcined in air at 0.88° C./hour from 250° C. to 600° C. and held for 9 hours. The temperature was then lowered to 350° C. and the sample reduced in carbon monoxide for ½ hour.

Following the chromium/MCM-41 catalyst reduction, the reaction temperature was lowered to 120° C. and 1-decene was fed at 1.91 LHSV. An oligomerization product was isolated and had a viscosity, at 40° C., of 2419 cS. Its viscosity measured at 100° C. was 238 cS. The calculated viscosity index was 237.

The reaction temperature was raised to 182° C. at 1.95 LHSV. Another product was isolated by distillation and its viscosity, at 40° C., was 197 cS. The viscosity, at 100° C., was 27.6 cS. The viscosity index was 178.

Figure 2:
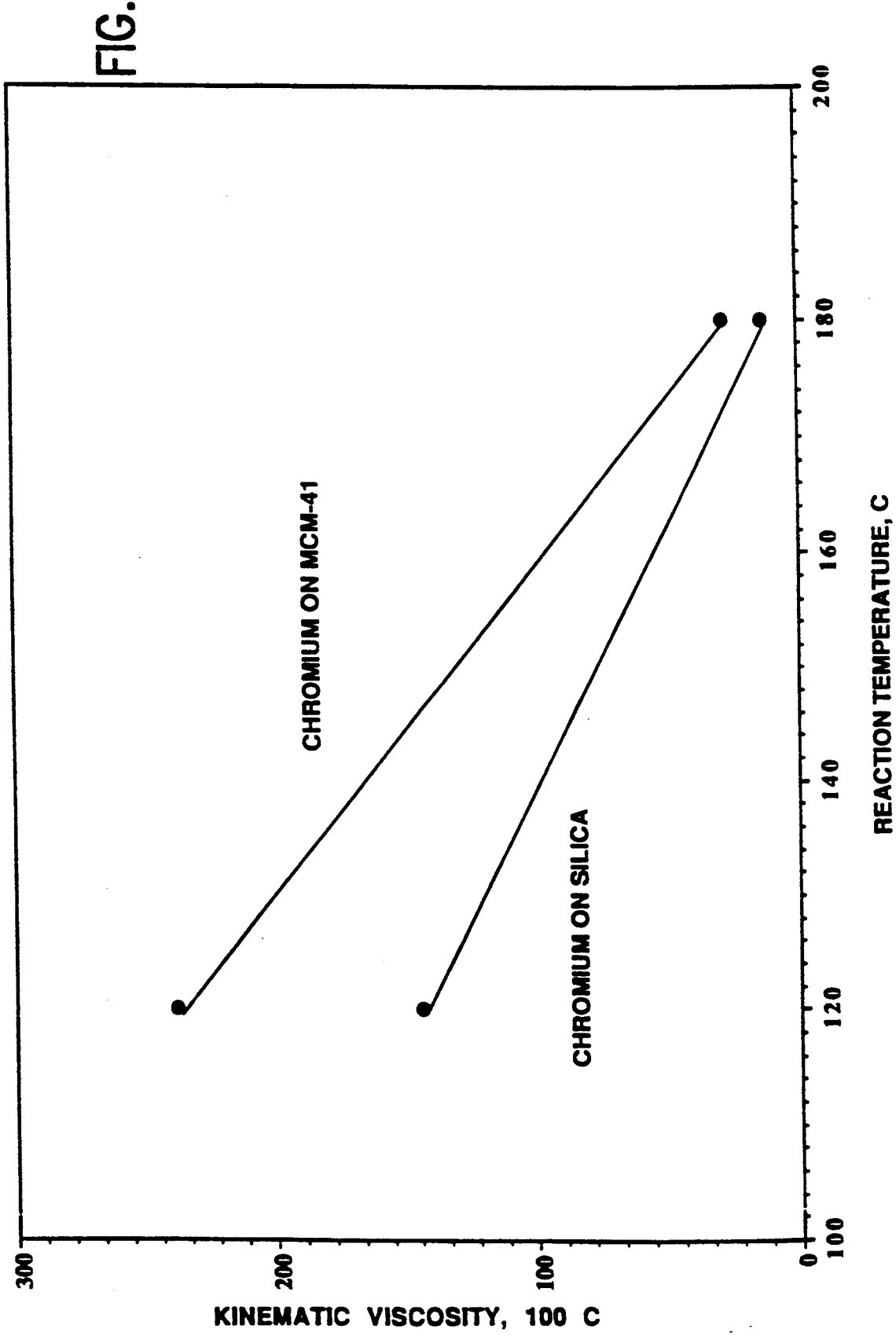

These viscosities, produced by the chromium/MCM-41 catalyst, are much greater than is expected by chromium on silica catalysts. The differences in viscosities between the two catalysts are shown in FIGS. 1 and 2 for viscosities measured at 40 and 100° C., respectively.

EXAMPLE 21

A crystalline support material was prepared in the manner described below.

One hundred grams of cetyltrimethylammonium (CTMA) hydroxide solution was combined with 20 grams of tetraethylorthosilicate (TEOS) with stirring at approximately 4° C. The stirring was continued for one hour. This mixture was placed in a polypropylene bottle and put into a steam box (~100° C.) for 48 hours. The mixture had a composition in terms of moles per mole $SiO_2$ assuming complete exchange of the surfactant:

0 59 moles of $(CTMA)_2O$
41 moles of $H_2O$

The mixture ratio of solvent/$(R'_2O+M_2O)$ was 82.

The resultant product was filtered, washed, air-dried and calcined (1 hour at 540° C. in flowing nitrogen followed by 6 hours in air). A tabulation of the X-ray diffraction peak positions of the calcined material, obtained by deconvolution of the diffraction pattern was as follows:

| Interplanar d-Spacing | Relative Intensity | $d_n/d_1$ |
|---|---|---|
| 33.1 | 100.0 | 1.00 |
| 28.6 | 12.3 | 0.86 |
| 21.7 | 1.2 | 0.66 |
| 20.3 | 1.1 | 0.61 |
| 18.1 | 3.8 | 0.55 |
| 17.3 | 6.0 | 0.52 |
| 16.5 | 2.3 | 0.50 |
| 15.9 | 1.6 | 0.48 |

This support material (1.93 g.) was added to a solution of chromium acetate made by dissolving 0.092 g. of chromium acetate (monohydrate) in 15 ml. water and left to stand overnight. The water was then evaporated and the resulting material dried in vacuum at 120° C. for 1 hour.

The chromium catalysts was placed in a fixed bed reactor and activated by heating in nitrogen at 250° C. for 4 hours, after which the catalysts was heated in air from 250° to 600° C. at about 1° C./min. After holding at 600° C. for about 8 hours, the temperature was reduced to 350° C. and the reactor flushed with nitrogen. At 350° C. carbon monoxide was allowed to contact the catalyst for ½ hour to reduce the chromium to the lower valent state.

The reduced chromium catalyst was used for the oligomerization of 1-decene under the conditions shown below in a fixed bed reactor.

| Run No. | 21-1 | 21-2 | 21-3 | 21-4 |
|---|---|---|---|---|
| Reactor Temp., °C. | 120 | 100 | 120 | 180 |
| LHSV | 0.84 | 0.84 | 0.90 | 0.88 |
| Recovery, % | 12 | 8 | 7 | 4 |
| KV, 40° C. | 368 | 732 | 475 | 30 |
| KV, 100° C. | 46 | 85 | 58 | 6 |
| VI | 182 | 204 | 191 | 174 |

We claim:

1. An olefin oligomerization catalyst which comprises a supported, reduced Group VIB metal oxide component on a support which comprises an inorganic, porous non-layered crystalline phase material exhibiting, after calcination, an X-ray diffraction pattern with at least one d-spacing greater than about 18 Å with a relative intensity of 100, and having a benzene adsorption capacity of greater than 15 grams benzene per 100 grams of the material at 50 torr and 25 ° C.

2. An olefin oligomerization catalyst according to claim 1 in which the inorganic, porous crystalline phase material has an X-ray diffraction pattern following calcination with at least two peaks at positions greater than about 10 Å d-spacing, at least one of which is at a position greater than about 18 Å d-spacing, and no peaks at positions less than about 10 Å d-spacing with relative intensity greater than about 20% of the strongest peak.

3. An olefin oligomerization catalyst according to claim 1 in which the crystalline phase material exhibits a hexagonal electron diffraction pattern that can be indexed with a $d_{100}$ value greater than about 18 Å.

4. An olefin oligomerization catalyst according to claim 3 in which inorganic, porous crystalline phase material has an X-ray diffraction pattern following calcination with at least one peak whose d-spacing corresponds to the $d_{100}$ value from the electron diffraction pattern of the material.

5. An olefin oligomerization catalyst according to claim 4 in which the crystalline material comprises the aluminosilicate having the structure of MCM-41.

6. An olefin oligomerization catalyst according to claim 1 in which the the X-ray diffraction pattern of the calcined material exhibits a peak $d_1$ at a position greater than about 18 Angstroms d-spacing and at least one additional weaker peak $d_n$ with d-spacing such that the ratios of these d-spacings relative to $d_1$ correspond to the ranges:

| d-Spacing, $d_n$, Angstroms | $d_n/d_1$ | Relative Intensity |
|---|---|---|
| $d_1, \geq \sim 18$ | 1.0 | 100 |
| $d_2$ | 0.87 ± 0.06 | w-m |

7. A catalyst composition according to claim 6 in which the X-ray diffraction pattern of the calcined material includes at least two additional weaker peaks at d-spacings $d_2$ and $d_3$ such that the ratios of these d-spacings relative to the strongest peak $d_1$ at a position greater than about 18 Angstroms d-spacing, correspond to the ranges:

| d-Spacing, $d_n$, Angstroms | $d_n/d_1$ | Relative Intensity |
|---|---|---|
| $d_1, \geq \sim 18$ | 1.0 | 100 |
| $d_2$ | 0.87 ± 0.06 | w-m |
| $d_3$ | 0.52 ± 0.04 | w |

8. An olefin oligomerization catalyst according to claim 1 wherein said crystalline phase material has a composition expressed as follows:

$$M_{n/q}(W_aX_bY_cZ_dO_h)$$

where M is one or more ions; n is the charge excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and $(a+b+c+d)=1$.

9. An olefin oligomerization catalyst according to claim 8 wherein a and d are 0 and h=2.

10. An olefin oligomerization catalyst according to claim 9 wherein X comprises aluminum and Y comprises silicon.

11. An olefin oligomerization catalyst comprising a reduced valence state chromium oxide on a support comprising an inorganic, porous crystalline phase material exhibiting, after calcination, an X-ray diffraction pattern with at least one d-spacing greater than about 18 Å and having a benzene adsorption capacity of greater than 15 grams benzene per 100 grams of the material at 50 torr and 25 ° C., having a hexagonal arrangement of uniformly-sized pores having diameters of at least about 13 Å, and exhibiting a hexagonal electron diffraction pattern that can be indexed with a $d_{100}$ value greater than about 18 Angstrom Units.

12. An olefin oligomerization catalyst according to claim 11 wherein said crystalline phase has an X-ray diffraction pattern following calcination with at least one peak whose d-spacing corresponds to the $d_{100}$ value from the electron diffraction pattern.

13. An olefin oligomerization catalyst according to claim 11 in which the crystalline phase material has an X-ray diffraction pattern with no peaks at positions less than about 10 Å d-spacing with relative intensity greater than about 20% of the strongest peak.

14. An olefin oligomerization catalyst according to claim 11 in which the crystalline phase material has an X-ray diffraction pattern with at least two peaks at positions greater than about 10 Angstrom Units d-spacing (8.842 degrees two-theta for Cu K-alpha radiation), at least one of which is at a position greater than about 18 Angstrom Units d-spacing.

15. An olefin oligomerization catalyst according to claim 11 wherein said crystalline phase has a composition expressed as follows:

$$M_{n/q}(W_aX_bY_cZ_dO)$$

where M is one or more ions; n is the charge excluding M expressed as oxides; q is the weighted molar average valence of M; n/q is the number of moles or mole fraction of M; W is one or more divalent elements; X is one or more trivalent elements; Y is one or more tetravalent elements; Z is one or more pentavalent elements; a, b, c, and d are mole fractions of W, X, Y, and Z, respectively; h is a number of from 1 to 2.5; and (a+b+c+d) =1.

16. An olefin oligomerization catalyst according to claim 15 wherein W comprises a divalent first row transition metal or magnesium; X comprises aluminum, boron, gallium or iron; Y comprises silicon or germanium; and Z comprises phosphorus.

17. An olefin oligomerization catalyst according to claim 15 wherein a and d are 0 and h=2.

18. An olefin oligomerization catalyst according to claim 15 wherein X comprises aluminum, boron, gallium or iron and Y comprises silicon or germanium.

19. An olefin oligomerization catalyst according to claim 11 in which the catalyst has been produced by oxidation of a chromium component on the support material at a temperature of 200° C. to 900° C. in the presence of an oxidizing gas and then by treatment with a reducing agent at a temperature and for a time sufficient to reduce said catalyst to a lower valence state.

20. An olefin oligomerization catalyst according to claim 19 in which the reducing agent comprises carbon monoxide.

* * * * *